United States Patent
Bowman et al.

[11] Patent Number: 6,135,944
[45] Date of Patent: Oct. 24, 2000

[54] METHOD OF INDUCING HARMONIOUS STATES OF BEING

[75] Inventors: Gerard D. Bowman, West Boylston; Edward M. Karam, Springfield; Steven C. Benson, Watertown, all of Mass.

[73] Assignee: Zebedee Research, Inc., West Boylston, Mass.

[21] Appl. No.: 09/187,591

[22] Filed: Nov. 6, 1998

Related U.S. Application Data

[60] Provisional application No. 60/065,851, Nov. 14, 1997.

[51] Int. Cl.[7] .................................................. A61M 21/00
[52] U.S. Cl. .............................................. 600/27; 600/28
[58] Field of Search ................................ 600/27, 28, 26

[56] References Cited

U.S. PATENT DOCUMENTS

| | | | |
|---|---|---|---|
| 4,834,701 | 5/1989 | Masaki | 600/28 |
| 4,883,067 | 11/1989 | Knispel et al. | 600/28 |
| 5,036,858 | 8/1991 | Carter et al. | 600/27 |
| 5,135,468 | 8/1992 | Meissner | 600/28 |
| 5,213,562 | 5/1993 | Monroe | 600/28 |
| 5,289,438 | 2/1994 | Gall | 600/28 |
| 5,356,368 | 10/1994 | Monroe | 600/28 |

OTHER PUBLICATIONS

"Chaos—Making A New Science", 1987 by James Gleick p. 293.

*Primary Examiner*—Max Hindenburg
*Assistant Examiner*—Brian Szmal

[57] ABSTRACT

A method of inducing harmonious states of being using vibrational stimuli, preferably sound, comprised of a multitude of frequencies expressing a specific pattern of relationship. Two base signals are modulated by a set of ratios to generate a plurality of harmonics. The harmonics are combined to form a "fractal" arrangement.

15 Claims, 6 Drawing Sheets

| Level | Harmonic Fractal Matrix | Frequency Ratio |
|-------|-------------------------|-----------------|
| 1 | $\begin{bmatrix} 3 & 5 \\ 30 & 50 \\ 300 & 500 \end{bmatrix}$ | $3/5 = 0.6$ |
| 2 | | $30/50 = 0.6$ |
| 3 | | $300/500 = 0.6$ |

| Whole Number Ratio | i | j | n | [Modulation] Multiplication Array |
|---|---|---|---|---|
| $R_1 = 1/1 = 1.0$ | 1 | 1 | 1 | $\begin{bmatrix} 1.0 \\ 1.33 \\ 1.5 \\ 2.0 \end{bmatrix}$ |
| $R_2 = 4/3 = 1.33$ | 4 | 3 | 2 | |
| $R_3 = 3/2 = 1.5$ | 3 | 2 | 3 | |
| $R_4 = 2/1 = 2.0$ | 2 | 1 | 4 | |
| $R_5 = 8/3 = 2.66$ | 8 | 3 | 5 | 2.66 |

FIG. 3A [4A]

| Level | Harmonic Fractal Matrix | | Frequency Ratio |
|---|---|---|---|
| | Carrier 1 | Carrier 1' | |
| 1 | $FC1 * R_1 = 144.0$ | $FC1' * R_1 = 151.85$ | $151.85/144.0 = 1.05$ |
| 2 | $FC1 * R_2 = 192.0$ | $FC1' * R_2 = 202.46$ | $202.46/192.0 = 1.05$ |
| 3 | $FC1 * R_3 = 216.0$ | $FC1' * R3 = 227.77$ | $227.77/216.0 = 1.05$ |
| 4 | $FC1 * R_4 = 288.0$ | $FC1' * R_4 = 303.70$ | $303.70/288.0 = 1.05$ |
| 5 | $FC1 * R_5 = 384.0$ | $FC1' * R_5 = 404.93$ | $404.93/384.0 = 1.05$ |

FIG. 5 ic fractal matrix 100 of the invention;

DETAILED DESCRIPTION OF THE PREFERRED EMBODIMENTS

Figure 2:
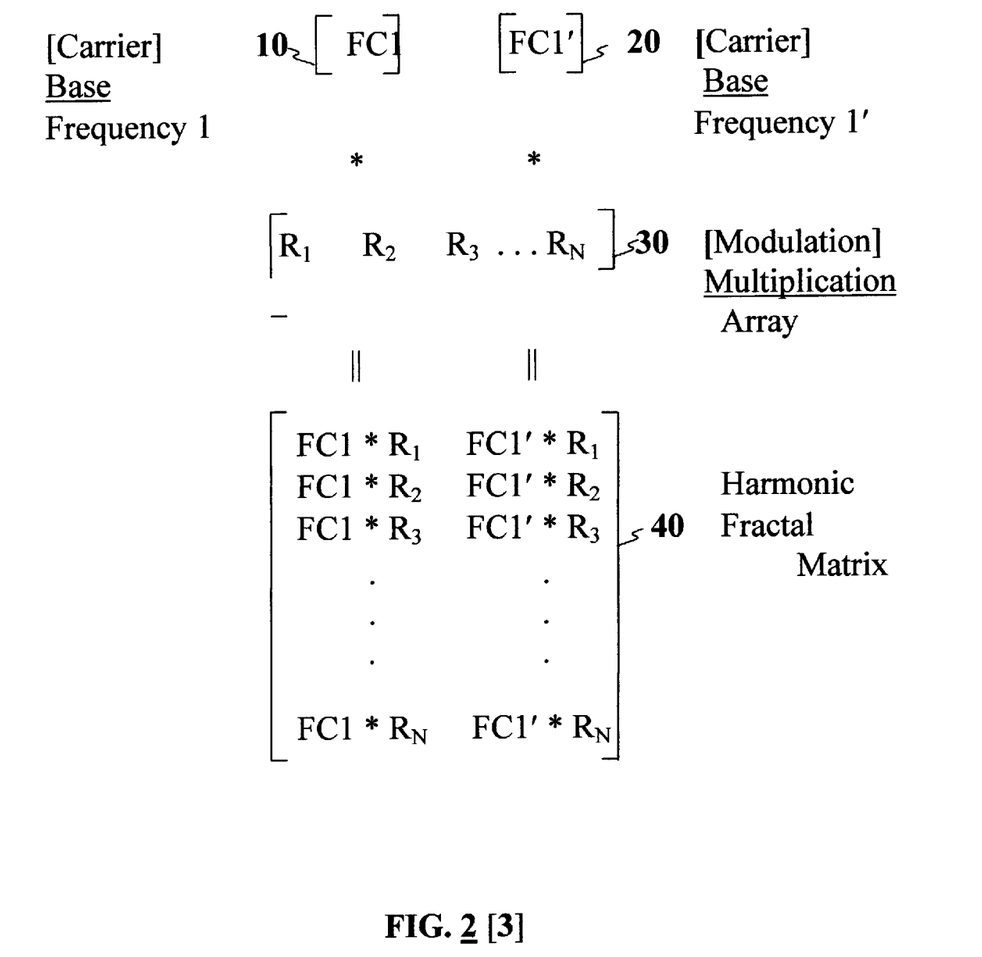

The application of vibrational stimuli comprised of harmonic relationships arranged to form specific patterns has been extensively investigated by the present inventors. As a result of that investigation, it was determined that stimuli comprised of harmonic frequencies arranged to express fractal relationships brought about profound changes in conscious perception, as well as psychological and physiological states of being. The method, according to a preferred embodiment of the present invention, derives from this discovery the fractal arrangement of frequency harmonics referred to as the "harmonic fractal matrix". FIG. 2 graphically illustrates the process by which the harmonic fractal matrix is generated. A base frequency 1 70 and a base frequency 1' 80 are operated upon by a multiplication array 90. The resulting harmonic frequencies produce the harmonic fractal matrix 100 as shown.

The detailed example below outlines each of the formulaic steps to create the harmonic fractal matrix using audio signals.

First, two audio base signals having frequencies $f_{C1}$, and $f_{C1'}$, are chosen such that the frequencies are separated by a non-zero value. An example of two such frequencies is given below.

| Base Signal 1 | Base Signal 1' |
|---|---|
| $f_{C1}$ = 144 Hz | $f_{C1'}$ = 151.85 Hz |

The separation frequency, $\Delta f_{C1}$, of 7.85 Hz used in this example is derived from the following equation.

$$\Delta f_C = 3\phi^2 = 7.85$$

Where $\phi$ is the mathematical "golden mean" (1.618), a ratio commonly found in nature and in esthetically pleasing Western works of art. Choosing a separation frequency based upon the golden mean has been found to produce beneficial results.

Second, a set of ratios of whole numbers is selected to comprise the elements of a multiplication array. These ratios are of the form expressed in the following equation.

$$R_n = \frac{i_n}{j_n}, \quad n = 1 \text{ to } N$$

where:

R=ratio;

i and j=positive integer values;

---

METHOD OF INDUCING HARMONIOUS STATES OF BEING

CROSS-REFERENCE TO RELATED APPLICATION

This application under 37 CFR §119 claims priority from U.S. Provisional Patent application Ser. No. 60/065,851 filed Nov. 14, 1997

FIELD OF THE INVENTION

This invention relates to applying stimuli to a human being to induce an altered state of consciousness.

BACKGROUND OF THE INVENTION

Throughout the ages music has demonstrated the ability for sound to influence an individual's state of being. Musicians have intuitively produced compositions that elicit a wide range of emotional response. The science of psychoacoustics explores the processes underlying this phenomena. The psychoacoustic theory of the present invention incorporates a scientific method of influencing an individual's state of being through sound.

Several methods for using sound to induce altered states of being have previously been explored. Most of these efforts have dealt with techniques that incorporate measured physiological data, primarily Electroencephalograph (EEG) signals, into a stimulus to be introduced to the body. Encoding EEG frequency information into an audio stimulus to induce specific brain wave frequencies is a technique commonly found. Typically, these techniques employ a single frequency or a plurality of frequencies that are varied over time to linearly guide the brain waves to a desired frequency of vibration. Several known techniques for inducing altered states using vibrational stimuli based upon EEG brain wave information are shown, for example, in the following U.S. patents:

| | | |
|---|---|---|
| 4,834,701 | 5,135,468 | 5,356,368 |
| 4,883,067 | 5,213,562 | |
| 5,036,858 | 5,289,438 | |

SUMMARY OF THE INVENTION

Figure 1:
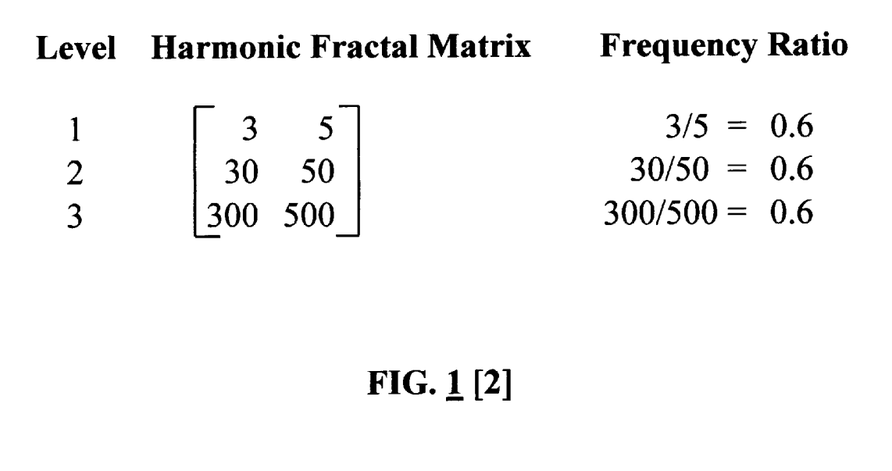
FIG. 1 illustrates a fractal frequency arrangement expressing the structured pattern of harmonic relationship of the harmonic fractal matrix according to the invention.

The present invention provides a method of inducing harmonious states of being through the application of vibrational stimuli, preferably sound. The stimuli are comprised of a pattern of waveforms that express what we call a "fractal" arrangement in their frequency relationships. FIG. 1 exemplifies such a fractal arrangement of harmonic frequencies. This arrangement is organized in matrix form and thus is referred to as a "harmonic fractal matrix". The ratio of 3 Hz to 5 Hz is in the same proportion as 30 Hz to 50 Hz and 300 Hz to 500 Hz. Each of these frequency pairs are said to be "fractally equivalent" to every other as they express the same proportion through varying levels of magnitude.

BRIEF DESCRIPTION OF THE DRAWINGS

The invention is described in greater detail hereinafter by reference to the accompanying drawings, wherein:

FIG. 2 graphically illustrates the process of multiplying carrier frequency 1 70 and carrier signal frequency 1' 80 by n=harmonic number counter (1,2,3, . . . N); and
N=total number of harmonics.

Figure 3A:
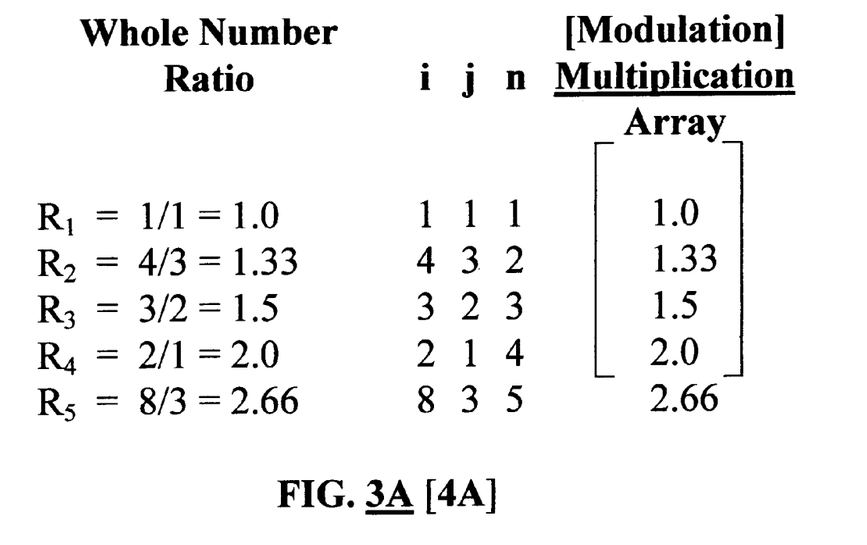
FIGS. 3A–3B show a detailed example of the modulation array and harmonic fractal matrix of FIG. 2 according to the invention.

FIG. 3A shows an example of a quintessential (N=5) multiplication array comprised of ratios.

Figure 3B:
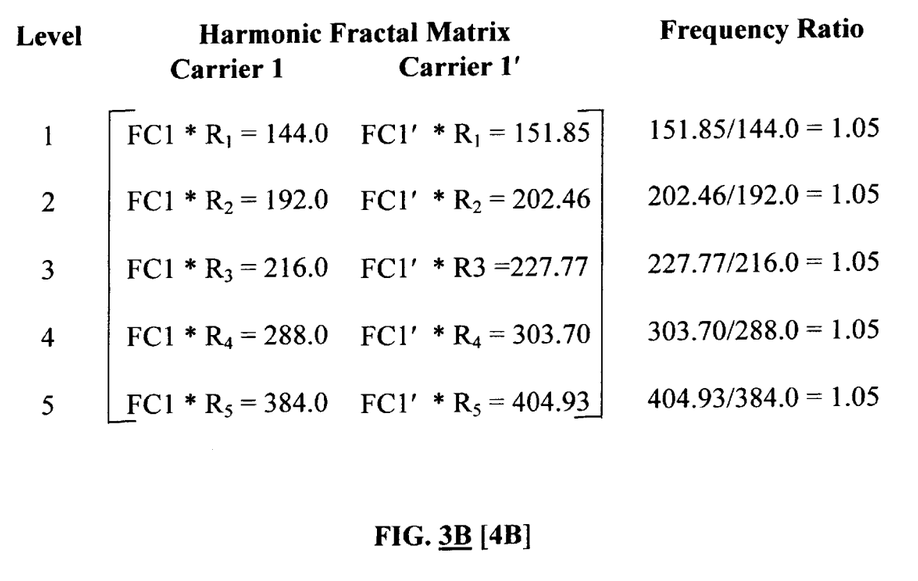

Third, the frequency of each base signal is multiplied by the multiplication array to produce a plurality of harmonic signals. FIG. 3B shows the result of applying the multiplication array of FIG. 3A to the base signal frequencies. As shown, the ratio that stands between the harmonic frequencies remains constant as the absolute frequency values are changed. This produces harmonics that relate to each other in a "fractally equivalent" nature. Thus the simultaneous application of base frequency 1 harmonics and base frequency 1' harmonics produces N simultaneous levels of fractally equivalent frequency relationships establishing the harmonic fractal matrix of FIG. 3B.

Another desired characteristic of this process is to apply the multiplication array as a dividing principle to the amplitudes of the base signals. The amplitudes of the harmonic signals are thus inversely related to their frequencies. In other words, the amplitude of a harmonic signal is decreased in the same proportion as its frequency is increased and vice versa.

Finally, the signals of the harmonic fractal matrix are combined for application to the human body. Base frequency 1 harmonics are combined to produce composite signal C1 while base frequency 1' harmonics are combined to create composite signal C1' as shown in the equations below.

$$C1 = \sum_{n=1}^{N} f_{C1} * R_n \qquad C1' = \sum_{n=1}^{N} f'_{C1} * R_n$$

Figure 4:
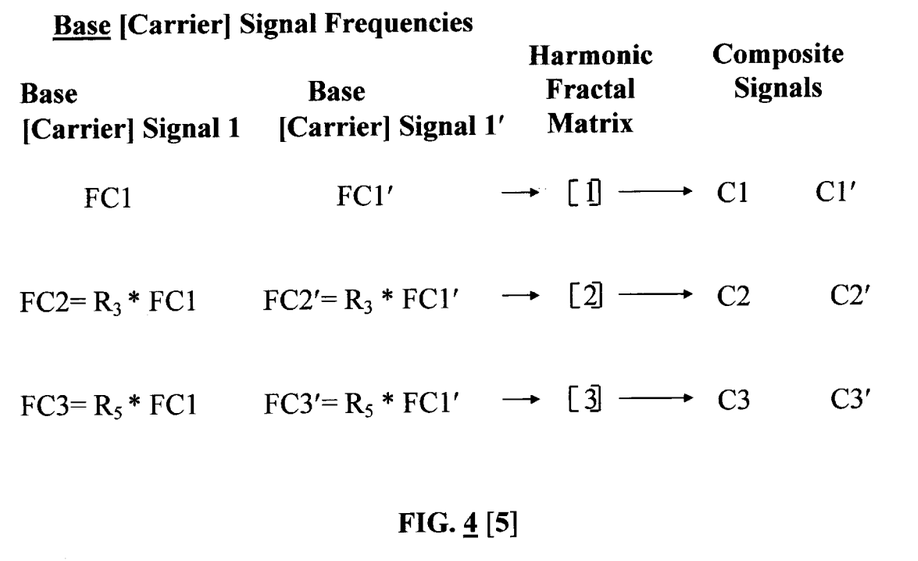
FIG. 4 illustrates the process by which a plurality of harmonic fractal matrices are created according to the invention.

The composite signals, C1 and C1', may be applied monaurally and/or binaurally to the ears to create varying effects. The aforementioned steps are preferably repeated a multitude of times to produce a plurality of harmonic fractal matrices. Each matrix is created using the same ratios applied to new and different base signal frequencies chosen from the original set of harmonic frequencies. FIG. 4 shows an example of creating two additional fractal matrices in which the original base frequencies are replaced by level 3 and level 5 harmonic frequencies.

Figure 5:
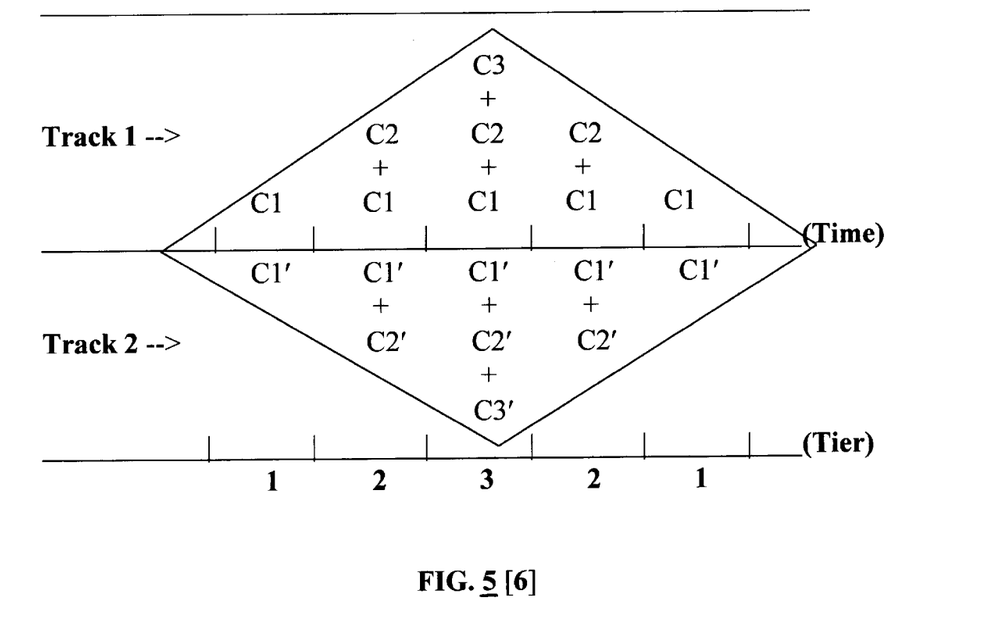
FIG. 5 illustrates an example of a multi-tiered pyramid arrangement outlining a template for combining and sequencing multiple harmonic fractal matrices according to the invention.

The composite signals of the harmonic fractal matrices may be applied simultaneously or preferably in stages to provide a gradual introduction of the stimulus to the body. FIG. 5 shows an example of a gradual introduction wherein the composite signals have been sequenced and mixed into two separate tracks. Here, the composite signals of a single matrix are initially applied, followed by the introduction of composite signals of additional matrices combined and sequentially arranged in time according to a multi-tiered pyramid arrangement. Tier 1 has C1 applied to track 1 while C1' is simultaneously applied to track 2. Tier 2 incorporates a mix of C1 and C2 to track 1 with a mix of C1' and C2' applied to track 2. Tier 3 includes a mix of C1, C2, and C3 to track 1 with a mix of C1', C2', and C3' applied to track 2. The duration of each tier is typically in the range of two to ten minutes, though shorter or longer durations may be used.

The multi-tiered pyramid arrangement is preferably introduced to the body by means of stereo audio signals applied to the ears. In one application, track 1 and track 2 are separately applied to the left and right channels, respectively. In another application, track 1 and track 2 are applied in a mix to both left and right channels in direct or inverse proportion to one of the whole number ratios.

The original base signals may be of a continuous or discontinuous nature. In a first embodiment continuous signals alone are used. In a second embodiment pulsated signals alone are utilized. In a third embodiment both continuous and pulsated signals are simultaneously utilized wherein the frequencies of the pulsated signals are either the same as, or are a whole number multiple of, the frequencies of the continuous signals. In this third embodiment, the continuous and discontinuous aspects are simultaneously applied to create an audible experience of a smooth melodic backdrop accompanied by the sounding of periodic pulses.

The method of the present invention has applications in a number of different areas. The induction of a natural state of harmony is marked by a reduction in muscle tension, reduced stress and anxiety, and an overall sense of well being. Variations in the base frequencies and ratios selected provide other desirable states including relief of mental tension and fatigue; induction of meditative states; heightened focus and concentration; enhanced dream activity and recall; and sleep induction. Other areas of application include aiding individuals with Attention Deficit Disorder (ADD) to remain calm and focused. The present invention further provides a method to positively influence the human body through non-intrusive, non-chemical, and inexpensive means, such as audio stimuli recorded on a cassette, which can be utilized at the discretion of the user.

The principles and preferred embodiments of the present invention have been described in the foregoing specification. The invention should not, however, be construed as limited to the particular forms described, or the particular examples given, as those are to be considered exemplary in nature and regarded as illustrative rather than restrictive. Variations and changes may be made by those skilled in the art without departing from the scope and pioneering spirit of the invention. Consequently, the invention should be considered as limited only by the scope of the appended claims.

What is claimed is:

1. A method of generating a combined signal, comprising:
   (a) selecting a first and a second base frequency, the first base frequency being different than the second base frequency;
   (b) providing a multiplication array having at least two elements;
   (c) multiplying the first and second base frequencies by each element of the multiplication array, thereby producing a plurality of respective first and second harmonic frequencies; and
   (d) combining the plurality of first harmonic frequencies to produce a first original composite signal and combining the plurality of second harmonic frequencies to produce a second original composite signal.

2. The method defined in claim 1, further comprising:
   (e) subjecting a human being to the first and second original composite signals.

3. The method defined in claim 2, wherein the first and second original composite signals are audio signals.

4. The method defined in claim 1, further comprising:
   (e) selecting one of the plurality of first harmonic frequencies as a substitute first base frequency and selecting one of the plurality of second harmonic frequencies as a substitute second base frequency;
   (f) repeating (c) and (d) using the substitute first and substitute second base frequencies, respectively, in place of the first and second base frequencies, thereby producing, respectively, a first and a second additional composite signal.

5. The method defined in claim 4, wherein the first and second original composite signals are not generated while the first and second additional composite signals are generated.

6. The method defined in claim 4, wherein the first and second additional composite signals are generated at least part of the time that the first and second original composite signals are generated.

7. The method defined in claim 6, further comprising:
(g) subjecting a human being to the first and second original composite signals and the first and second additional composite signals.

8. The method defined in claim 7, wherein the first and second original composite signals and the first and second additional composite signals are audio signals.

9. The method defined in claim 8, wherein the difference between the first base frequency and the second base frequency is 7.85 Hz.

10. A recording, comprising a playback medium storing at least first and second tracks of data representing, respectively, first and second composite signals, wherein:
(a) the first and second composite signals comprise, respectively, a combination of a first and a second plurality of harmonic frequenceies;
(b) each of the first and second plurality of harmonic frequencies is a product of a respective first and second base frequency and a ratio of positive integers; and
(c) the first base frequency is unequal to the second base frequency.

11. The recording defined in claim 10, wherein the first and second composite signals are audio signals.

12. The recording defined in claim 11, wherein the first base frequency differs from the second base frequency by 7.85 Hz.

13. A harmonic fractal matrix of frequencies, comprising a first and a second column of elements, wherein:
(a) both columns contain an equal number of elements;
(b) each element represents a frequency;
(c) each element of the first column is a product of a first base frequency and an element of a multiplication array;
(d) each element of the second column is a product of a second base frequency and an element of the multiplication array; and
(e) the first base frequency is unequal to the second base frequency.

14. The harmonic fractal matrix defined in claim 13, wherein each element of the multiplication array is a ratio of two positive integers.

15. The harmonic fractal matrix defined in claim 14, wherein the first base frequency differs from the second base frequency by 7.85 Hz.

* * * * *

UNITED STATES PATENT AND TRADEMARK OFFICE
CERTIFICATE OF CORRECTION

PATENT NO. : 6,135,944
APPLICATION NO. : 09/187591
DATED : October 24, 2000
INVENTOR(S) : Bowman et al.

It is certified that error appears in the above-identified patent and that said Letters Patent is hereby corrected as shown below:

On the title page: Item [75] First Inventor name should read Gerard David Bowman.

Signed and Sealed this

Fourteenth Day of October, 2008

JON W. DUDAS
*Director of the United States Patent and Trademark Office*